US010130097B2

(12) United States Patent
Meier et al.

(10) Patent No.: US 10,130,097 B2
(45) Date of Patent: Nov. 20, 2018

(54) ANTIMICROBIAL GLASS COATING

(71) Applicant: Glas Troesch Holding AG, Buochs (CH)

(72) Inventors: Pascal Meier, Zofingen (CH); Walter Haag, Grabs (CH); Andriy Romanyuk, Solothurn (CH)

(73) Assignee: GLAS TROESCH HOLDING AG, Buochs (CH)

( * ) Notice: Subject to any disclaimer, the term of this patent is extended or adjusted under 35 U.S.C. 154(b) by 0 days.

(21) Appl. No.: 15/433,226

(22) Filed: Feb. 15, 2017

(65) Prior Publication Data
US 2017/0231229 A1 Aug. 17, 2017

(30) Foreign Application Priority Data

Feb. 15, 2016 (EP) .................................... 16155752

(51) Int. Cl.
*A01N 59/20* (2006.01)
*C03C 17/22* (2006.01)
*C23C 14/00* (2006.01)
*C09D 5/14* (2006.01)
*C23C 14/06* (2006.01)
*A01N 25/08* (2006.01)
*C03C 17/245* (2006.01)
*C03C 17/23* (2006.01)
*C03C 17/34* (2006.01)
*C03C 17/42* (2006.01)
*C23C 14/08* (2006.01)
*C23C 14/34* (2006.01)
*C03C 17/00* (2006.01)
*C09D 1/00* (2006.01)

(52) U.S. Cl.
CPC ............ *A01N 59/20* (2013.01); *A01N 25/08* (2013.01); *C03C 17/007* (2013.01); *C03C 17/22* (2013.01); *C03C 17/225* (2013.01); *C03C 17/23* (2013.01); *C03C 17/245* (2013.01); *C03C 17/3411* (2013.01); *C03C 17/42* (2013.01); *C09D 1/00* (2013.01); *C09D 5/14* (2013.01); *C23C 14/0036* (2013.01); *C23C 14/0641* (2013.01); *C23C 14/0676* (2013.01); *C23C 14/0682* (2013.01); *C23C 14/087* (2013.01); *C23C 14/3414* (2013.01); *C23C 14/3464* (2013.01); *C03C 2217/24* (2013.01); *C03C 2217/281* (2013.01); *C03C 2217/29* (2013.01); *C03C 2217/70* (2013.01); *C03C 2217/734* (2013.01); *C03C 2217/76* (2013.01); *C03C 2218/155* (2013.01)

(58) Field of Classification Search
None
See application file for complete search history.

(56) References Cited

U.S. PATENT DOCUMENTS

| | | | |
|---|---|---|---|
| 2009/0162695 A1 | 6/2009 | Hevesi et al. | |
| 2013/0252021 A1* | 9/2013 | Neumann | ............... A61L 27/06 428/657 |
| 2015/0208664 A1* | 7/2015 | Borrelli | .................. A01N 59/20 424/411 |

FOREIGN PATENT DOCUMENTS

| | | | |
|---|---|---|---|
| DE | 102005013857 A1 | | 9/2006 |
| DE | 102006060057 A1 | | 6/2008 |
| DE | 102010054046 A1 | * | 6/2012 |
| DE | 102010054046 A1 | | 6/2012 |
| EP | 2392690 A1 | | 12/2011 |

OTHER PUBLICATIONS

Chiu et al., "Antibacterial property of CuCrO2 thin films prepared by RF magnetron sputtering deposition", Vacuum 87: 174-177 (2013).*
Kamimura et al., "Preparation of Cuprous Oxide (Cu2O) Thin films by Reactive DC Magnetron Sputtering", Vacuum 87: 174-177 (2013).*
Chiu et al., "Antibacterial property of CuCrO2 thin films prepared by RF magnetron sputtering deposition", Vacuum 87: 174-177 (2013) (Year: 2013).*
Extended European Search Report for EP App No. 16155752.5 dated Jul. 25, 2016, 9 pgs.
Chiu, T-W., et al., Antibacterial Property of CuCrO2 Thin Films Prepared by RF Magnetron Sputtering Deposition, Vacuum, 2013, 87, pp. 174-177.
Kamimura, K., et al., Preparation of Cuprous Oxide (Cu2O) Thin Films by Reactive DC Magnetron Sputtering, IEICE Transactions on Electronics, Feb. 2004, E87-C(2), pp. 193-196.
Nosaka, T., et al., Copper Nitride Thin Films Prepared by Reactive Radio-Frequency Magnetron Sputtering, 1999, Thin Solid Films, 348, pp. 8-13.

* cited by examiner

*Primary Examiner* — Thor Nielsen
(74) *Attorney, Agent, or Firm* — Procopio, Cory, Hargreaves & Savitch LLP

(57) ABSTRACT

The invention relates to an object having a coating arranged on at least one surface of the object, which comprises at least one antimicrobially active layer having an antimicrobial agent, wherein the agent comprises a copper (I) compound and/or a copper (II) compound.

14 Claims, No Drawings

ANTIMICROBIAL GLASS COATING

CROSS-REFERENCE TO RELATED APPLICATIONS

This U.S. non-provisional patent application claims priority under 35 U.S.C. § 119 of EP Patent Application No. 16155752.5, filed on Feb. 15, 2016, the entire contents of which are hereby incorporated by reference.

The invention relates to an object provided with an antimicrobial layer, in particular with an antibacterial layer, according to the preamble of claim 1, and a method for coating an object with an antimicrobial layer, in particular an antibacterial layer, according to claim 10.

Various methods for providing different surfaces with antimicrobial properties are known from the prior art.

For example, US 2015/0225288 A1 discloses a method for introducing silver ions into the surface of a glass substrate by way of a sequence of chemical baths disclosing metal ions replaceable via ion exchange.

On the other hand, EP 1 828 071 B2 discloses a method for producing a glass substrate, which is coated using a mixed layer made of an antimicrobial active ingredient and a binder material by a sputtering process.

In principle, very different substrates can be provided with corresponding properties.

One object of the present invention is to provide an object, which has a particularly effective antimicrobial coating of at least one surface with good adhesion, even in the case of a dry surface. A further object of the invention is to provide a transparent object, which has a corresponding antimicrobial coating having particularly good optical properties. The antimicrobial effect, in particular the antibacterial effect, is to develop in a short time in this case, so that a majority of the microorganisms are already eliminated within an hour.

Furthermore, it is an object of the invention to disclose a method, by means of which one or more surfaces of objects of differing geometries can be provided cost-effectively with a corresponding antimicrobial coating. In this case, the method is to be suitable in particular for coating large-area, for example, substantially planar substrates and/or for the high-quality optical coating of surfaces.

Various objects, the surface or surfaces of which can be coated using the corresponding method, and corresponding fields of use are mentioned solely as an exemplary selection hereafter:

Display glasses, display glass covers; inserts, panels, or complete surfaces of ticket machines and ATMs; elevator panels, light switches, control elements, automobile cockpits, medical packaging systems; inserts, panels, covers, attachments, fronts, or entire surfaces of walls, doors, shelves, furniture (bookshelves, tables), kitchens, bathrooms, showers, mirrors; in this case, in particular corresponding objects as they are used in public facilities and/or hospitals.

At least one of the above-mentioned objects or a combination thereof is advantageously achieved by independent claim 1 or 10.

Thereby, an object having a coating arranged on at least one surface of the object has at least one antimicrobially active layer, which comprises a copper (I) compound and/or a copper (II) compound as an antimicrobial agent. The antimicrobial agent can be an oxide, an oxynitride, or a nitride in this case. The agent is preferably a copper (I) compound, because such compounds, in particular $Cu_2O$ and $Cu_3N$, have been shown to be particularly effective in this case.

The copper-containing compound is provided in this case in the layer in a concentration such that it comprises at least 2 at % copper, preferably at least 6 at % copper.

Thereby, the layer can contain in addition to copper, silicon, nitrogen, oxygen, and optionally one or more doping elements D, or can be synthesized from these elements. Advantageously, at least 25 at % silicon, at least 40 at % nonmetals, for example, at least 15 at % nitrogen and at least 25 at % oxygen, and the doping element or elements D in total in a range from $0 \leq D \leq 15$ at % are contained in the layer. The respective upper limits result in this case in accordance with the total of the lower limits of the other elements subtracted from 100%, for example, 35 at % for copper or 58 at % for silicon, respectively. However, preferably not more than 15 at % copper, not more than 45 at % silicon, not more than 31 at % nitrogen, not more than 45 at % oxygen, and not more than 10 at % D are incorporated into the layer. This is true in particular if a ratio $$G=(Cu+Si)/(Cu+Si+N+O+D)$$

of all elements contained in the antimicrobial layer of $32 \leq G \leq 52$ at % was additionally set in this case.

The setting of at least one of the following ranges (all specifications in at %) has been shown to be a range of the respective element-related layer composition which is favorable both with respect to the antimicrobial properties and also the optical properties, which are particularly significant for coating glasses, as will be discussed below in detail in the examples: $6 \leq Cu \leq 8$, $33 \leq Si \leq 37$, $21 \leq N \leq 25$, $32 \leq O \leq 38$, $D \leq 3$, and $37 \leq G \leq 47$. It has been shown in this case that setting one particularly favorable range in combination with the further above-mentioned larger ranges relevant according to the invention is already advantageous, but these can also be combined individually or freely with one another depending on the intended application. Thus, for example, to provide the layer with particularly good adhesive properties, the silicon and oxygen content of at least one layer surface can be increased in the scope of the Cu/(Cu+Si) ratio I disclosed according to the invention, or in the scope of the O/(O+N) ratio H disclosed according to the invention, respectively, to increase the edge or surface regions of the layer occupied by $SiO_2$ molecules or clusters. Alternatively, layer surface regions which are placed directly on the substrate or on the surface of the substrate or the intermediate layer can also be formed as pure $SiO_2$ layers. If needed, the layer transition to or from the antibacterial layer can be formed graduated in each case.

The thickness d of the antimicrobial layer was set in this case in a range from $1 \leq d \leq 130$ nm, preferably from $5 \leq d \leq 80$ nm, particularly preferably from $10 \leq d \leq 50$ nm.

The object can consist, at least on the surface, of metal, plastic, ceramic, or glass in this case.

The following elements, in particular metals, can be used either individually or in combination as the doping element D: Ag, Al, As, Cd, Cr, Fe, Mn, Ni, Sn, Zn. The following properties can thus be influenced in a targeted manner, inter alia.

Color: by adding Cr, Mn, Ni, Sn, or Zn;
corrosion resistance: by adding Al, As, Cr, Fe, Mn, Ni, Sn;
wear resistance: by adding Ag, Al, Cd, Sn.

Thereby, the corrosion and wear resistance can be adjusted as can be the adhesion of the layer and/or the suitability thereof for an additional coating, by the silicon content.

Furthermore, at least one intermediate layer can be arranged between the layer and the surface, for example, to improve the adhesion, for graduated adaptation of the index of refraction, to create an antireflective (AR) layer, or the like. Alternatively or additionally, in a further embodiment of the invention, a hydrophobic and/or oleophobic layer, a so-called "easy-to-clean layer", can be arranged on the layer surface, to facilitate the cleaning of the object. It can be synthesized from fluorosilanes, for example. Such layers provide substantial advantages, because therefore fewer microbial pathogens already reach the surface from the beginning, so that a fluorosilane layer reduces the number of bacteria transferred by touching the surface with the hand by 60%, for example. It has been recognized in this case that it adheres particularly well to the $SiO_2$-rich surface regions of the layer, which are always provided on the surface due to the setting of the Cu/(Cu+Si) I according to the invention. In addition, the coating process can also be controlled so that, during the deposition of the antibacterial layer on the surface thereof, if needed, for example, connected thereto via a gradient layer, a $SiO_2$-richer layer can be formed, for example, by adjusting the ratio 5≤I≤15 at %, which is used as the adhesive layer for the fluorosilane layer, without having to lose or greatly weaken the antimicrobial properties in this case. Additionally or alternatively, such an adhesive layer can also be provided as an intermediate layer, wherein in this case a pure $SiO_2$ layer can also be provided as an adhesive layer.

In a further embodiment of the invention, the object is a glass, wherein glass is meant here in its most general meaning and therefore also comprises, in addition to the typical inorganic or mineral glasses, organic glasses made of polymer materials, for example, polymethyl methacrylate (PMMA), polycarbonate (PC), CR39, or other suitable polymers and polymer mixtures.

In particular for objects made of glass, the intermediate layer can comprise an antireflective layer, which comprises at least one high-refractive-index and/or one low-refractive-index layer film. For higher optical demands, however, an antireflective layer made of at least two high-refractive-index and two low-refractive-index layer films can preferably be used. Additionally or alternatively, an antireflective layer consisting of at least one high-refractive-index and one low-refractive-index layer film, in this case preferably of at least two high-refractive-index and two low-refractive-index layer films, can also be arranged on a surface of the object opposite to the antibacterial layer.

The high-refractive-index layer can comprise, for example, $TiO_2$, $Nb_2O_5$, $Si_3N_4$ and the low-refractive-index layer can comprise, for example, $SiO_2$, ZnO, $SnO_2$, $ZnSnO_3$, $ZrO_2$ and/or can consist of at least one of these materials.

To optimize the layer properties, in particular on glass, the layer should contain not more than 8 at % Cu, not more than 37 at % Si and not more than 25 at % N and not more than 38 at % O, whereby optimum optical properties for the layer can be ensured.

A further object of the invention is to provide a method for coating an object with at least one antimicrobial layer, in particular one antibacterial layer. Such a method comprises at least the following steps:

providing a sputtering facility having at least one copper-containing target;
introducing the object into the sputtering facility;
creating a vacuum in the sputtering facility;
introducing an inert sputtering gas and a reactive gas containing oxygen and/or nitrogen;
igniting and maintaining a sputtering discharge at the target;
setting the reactive gas flow so that a layer containing a copper (I) compound and/or a copper (II) compound, in this case preferably an oxide, an oxynitride, and/or a nitride of copper is deposited on the object.

Preferred reactive gases are oxygen and/or nitrogen in this case.

Furthermore, one of a copper (I) compound, in particular one of $Cu_2O$ and $Cu_3N$, is preferably deposited in this case.

In one method variant, at least one CuSi target and/or one CuSiN target is used, wherein a ratio $I_T$=Cu/(Cu+Si)

in the target is provided in a range from 5≤$I_T$≤40 at %, thereby preferably in a range from 15≤$I_T$≤30 at %. In this case, the elements copper and silicon can be provided in the target in metallic form, in partially oxidized form, or in fully oxidized form, for example, as a nitride, oxide, or oxynitride, for example, as $Cu_2O$, $Cu_3N$, CuO, $SiO_2$, $Si_3O_4$, $Cu_aSi_bN_cO_d$, $Cu_eSi_fN_g$, $Cu_hSi_iO_j$, or as the mixed oxides, mixed nitrides, or mixed oxynitrides thereof. The coefficients a to j can be set corresponding to one or more compounds or also corresponding to substoichiometric or superstoichiometric amounts in this case. For example, if a layer having very high or exclusively copper (I) component is to be deposited, for example, a target synthesized from one or more copper (I) compounds can be used. Alternatively, targets having a component of metallic copper and a component of one or more copper (I) and/or copper (II) compounds can also be used, whereby, depending on the setting of the process parameters, either layers which contain metallic copper and also copper (I) or copper (II) compounds or, for example, with higher oxygen and/or nitrogen component in the process gas, also $Cu_aSi_bN_cO_d$ layers which contain exclusively oxidized copper compounds can be deposited.

In addition, the setting of the partial pressure of the oxygenated gas and the partial pressure of the nitrogenous gas can be adjusted in this case so that a ratio H=N/(N+O) of 30≤H≤50 at % is provided in the layer. This can be performed, for example, after initial setting of the gas flows to desired starting values, by a regulation of the gas flows by means of a process-accompanying measurement of the respective layer composition, wherein the respective measured nitrogen content or oxygen content in the layer is used to regulate the corresponding gas flow. Corresponding methods are known to a person skilled in the art in the field of coating technology.

Surprisingly, the equilibrium may be shifted in favor of the formation of $Cu_2O$ instead of CuO by this adjustment of the nitrogen/oxygen ratio. The formation of the copper (I) compound, which is more active with respect to its antimicrobial or antibacterial effect, is thus preferred over the less strongly active copper (II) compound, whereby in spite of a comparatively low copper concentration, a high antimicrobial or antibacterial effect can be achieved. At the same time, the oxygen content is not to be set lower, because otherwise index of refraction and absorption of the layer increase, which is disadvantageous at least for coating conventional glasses.

The mixed targets can be produced in this case in different ways, for example, by smelting methods or by powder-metallurgy methods, wherein the latter are suitable for the production of greatly differing target compositions, because the starting materials (Si, $SiO_2$, $Si_3N_4$, Cu, $Cu_2O$, $Cu_3N$, etc., see above) may be arbitrarily mixed and pressed. The HIP method (hot isostatic pressing), which is particularly suitable for planar target geometries, and also various thermal spraying methods, such as flame spraying, arc spraying, plasma spraying, and vacuum plasma spraying, which are also very well suitable for the production of, for example, cylindrical tubular cathodes, are listed here as examples of powder-metallurgy methods which can be used for producing targets.

Alternatively, mosaic or graft targets can also be used, in which, at least in the region of the surface to be sputtered away, for example, of a Si or $Si_3N_4$ target, Cu or $Cu_3N$ graftings or inlays are introduced.

Such a method is advantageous for industrial production, because the regulation effort is low as a result of the substantially consistent Cu/Si ratio of the sputtered CuSi material and planar or also three-dimensional substrates can be continuously coated, for example, by means of in-line facilities.

Alternatively, such a method for coating an object with at least one antimicrobial or antibacterial layer can also be executed on a sputtering facility having at least one copper target, a target containing copper (I), for example, $Cu_3N$ and/or $Cu_2O$, a target containing copper (II), for example, CuO and/or $Cu_3N_2$, or a target containing both oxidation levels of copper, and at least one silicon target, a target containing a silicon oxide, for example, $SiO_2$, and/or a target containing a silicon nitride, for example, $Si_3N_4$, wherein the copper-containing and silicon-containing targets are aligned, for example, both overlapping to the surface to be coated.

The individual steps of the method are the same in this case as described above, wherein, however, a setting or regulation of the sputtering rates, for example, on the copper target and on the silicon target additionally has to be performed, to set a ratio $$I=Cu/(Cu+Si) \text{ of } 5 \leq I \leq 30 \text{ at \%}$$

in the layer. The regulation of the sputtering rates can be performed in this case similarly to the regulation of the gas flows by means of a process-accompanying measurement of the respective layer composition, wherein the respective measured copper or silicon content in the layer is used to regulate the corresponding gas flow.

A further method alternative results, in which the object to be coated, as in the first method example, can also be coated by a single target, if, instead of a planar magnetron having a SiCu-containing target, a tubular target, which is rotatable about the cylinder axis, of a sputtering source is used. If the tubular target having a specific, for example, the above-mentioned Cu/Si composition, is additionally arranged between the object and a further sputtering source, the material composition of the rotating surface of the tubular target can be intentionally varied by turning the further sputtering source on/off and if desired by regulating it. The further sputtering source is optically separated in this case, at least by the sputtering source having the rotating tubular target, from the chamber in which the object is coated and can in turn, for example, be embodied as a planar magnetron source or as a further tubular magnetron source.

The sputtering source having the rotating target is designed in this case in relation to the coating chamber as the magnetron to coat the object and can in turn be coated on the side facing away from the coating chamber by the further sputtering source. Layer gradients, stepped changes, for example, of the copper/silicon content, of the content of the doping element or elements, or also only a consistent content, which is settable differently from batch to batch, however, of one or more doping elements on the surface of the object to be coated can thus also be produced, for example, similarly as in the method having two overlapping sputtering sources directed onto the object, depending on the material selection of the tubular target and the target of the further sputtering source.

Such methods have advantages, if layers having differing Cu/Si ratio are to be produced alternately, but require a higher effort of process adjustment.

Additionally, for example, a metallic adhesive layer made of copper or a $SiO_2$ adhesive layer can be created on the surface of the object, in that, for example, in a in-line facility, firstly the object passes through a coating station operated with corresponding target, for example, made of copper, silicon, or silicon oxide, and suitable sputtering or process gas setting.

Depending on the method used, in this case either the sputtering power of the at least one CuSi-containing target or the sputtering power of the copper-containing target and the sputtering power of the silicon-containing target can be adapted to the setting of the partial pressure, for example, of the $O_2$ and the $N_2$, so that a ratio $$G=(Cu+Si)/(Cu+Si+N+O) \text{ of } 32 \leq G \leq 52 \text{ at \%}$$

or $$G=(Cu+Si)/(Cu+Si+D+N+O) \text{ of } 32 \leq G \leq 52 \text{ at \%}$$

is set in the layer. The setting of the partial pressure can also be performed in this case by differential pressure measurement, but is generally regulated by the substantially simpler setting of the corresponding gas flows, wherein typically only the total process pressure is measured.

The reactive gas can in any case also be introduced only after introducing the inert sputtering gas and after the ignition of the target or targets. This is performed, for example, to clean the target surface before beginning the coating behind closed screens and/or to apfilm a metallic adhesive layer. The layer transition can in this case, as also in the other above-mentioned multilayer coatings, either be produced as stepped, for example, in the individual films of an AR layer, or graduated, for example, for the flowing transition of an adhesive layer.

Before the discussion of the invention on the basis of examples, firstly the measurement method used for establishing the antimicrobial efficacy, in particular the bactericidal efficacy of the layer will be explained, for which a test based on the "Test Method for Efficacy of Copper Alloy Surfaces as a Sanitizer" of the United States Environmental Protection Agency (EPA) was used. The corresponding EPA method refers to the version valid on 16 Jul. 2013, which was loaded from the following website: http://www.epa.gov. This method is particularly suitable for establishing the antimicrobial efficacy of dry copper-containing surfaces having high and rapidly acting antimicrobial effect, while in contrast the method set forth, for example, in EP1828071, according to norm JIS Z 2801, tests antibacterial glasses in a damp environment in a 24-hour cycle and is therefore less suitable for the present purpose for several reasons.

The test method used will be described hereafter:
Material Used:
  bacteria culture of the corresponding species
  sterilized water
  FCS (fetal calf serum)
  test surface
  agar plates
  Approach for determining the colony-forming unit (CFU) of a culture of the bacterial species to be studied after spreading, air drying, and replicating by means of plate culture: serial dilution of the bacteria by the factor $10^2$, $10^3$, $10^4$, $10^5$ in 20 µl water with 5% FCS and spreading onto a 2×2 cm reference glass, followed by 1 hour air drying and replication by means of plate culture. A good value for the antimicrobial activity test is in the range between $1\times10^2$-$3\times10^2$ CFU (i.e., bacteria and/or other microorganisms) per sample and enables a reliable detection of a 50% to 95% efficacy (killing rate). Remark: using a photometer, the bacteria density can be determined at $OD_{600}$ (i.e., absorption at 600 nm wavelength), wherein one unit corresponds to approximately $10^9$ bacteria.

Sequence Details

The bacteria culture is cultivated overnight and the concentration is determined. The bacteria are diluted in sterile water containing 5% FCS. The FCS is used as an organic impurity to simulate a contamination and helps to moisten the surface. The series dilution in water containing 5% FCS is applied to achieve the desired final dilution (see above). 20 µl of the obtained suspension are distributed homogeneously onto 2×2 cm sample surfaces and dried in ambient air. Untreated glass plates are used as the reference sample. After 60 minutes, the bacteria are transferred by moderate, 10-second pressing of the sample plates onto agar contact plates.

After incubation overnight at 37° C., the surviving bacterial colonies are counted and the antimicrobial effect of the coated sample is calculated in comparison to an uncoated sample.

The determination of the quantity components of the layer elements (Cu, Si, N, O, D) and the ratios (G, H, I) calculated therefrom, as well as the determination of the oxidation number(s) of the elements present in the layer, for example, copper (I) or copper (II) was performed by X-ray photoelectron spectroscopy (XPS). A monochromatic Al—K-alpha (1486.6 eV) X-ray source was used to determine the surface integral of the Cu 2p 3/2, the Si 2p, the O is, and the N is signals.

Individual aspects of the invention will be explained in detail hereafter on the basis of examples and tabulated range specifications.

To produce sample plates, pre-cleaned glass plates were inserted into the holder of a PVD sputtering facility and airlocked into the facility. The sputtering facility, which is equipped with two sputtering sources (planar magnetrons), which are aligned on a planar coating plane, overlapping with respect to the atomization cone thereof, was equipped for this purpose with a copper target and a silicon target. After generating a vacuum and setting a sputtering pressure, in a range from $0.10 \leq p \leq 0.30$ Pa by introducing inert gas (for example, Ar), the sputtering cathodes were ignited and therefore cleaned of possible oxidic residues. Subsequently, by additionally introducing nitrogen and oxygen in a respective desired ratio, the process pressure was preset in a range from $0.2 \leq p \leq 0.4$ Pa and the power of the targets was regulated in accordance with the desired Cu/Si ratio and the desired layer thickness. A surface of the glass was then subjected to the sputtering plasma and coated. Subsequently, the glass plates were airlocked out of the facility, isolated to form sample plates, and the antimicrobial efficacy was determined in accordance with the above-described test sequence using different species.

In addition, the optical properties of a 4-mm-thick normal glass (soda-lime glass) coated similarly to the test plates or the glass plates was determined after the coating according to CIE Lab System using light type C at an observation angle of 2°.

An example (ex.) of the presets for a coating process is provided hereafter, using which particularly good antimicrobial and optical layer properties were able to be achieved:

Gas Flows:
Ar: approximately 200 sccm
$N_2$: approximately 100 sccm
$O_2$: approximately 9 sccm The exact gas flows were automatically tracked by determining the quantity components measured during the coating process and using the corresponding data for fine regulation of the flow.

The power on the copper target was set in this case to 0.32 W/cm², and the power on the silicon target was set to 5.88 W/cm².

A 40-nm-thick layer having the following composition was thus deposited:

Cu: 7 at %, Si: 35 at %, N: 23 at %, O: 35 at %
(G=42 at %, H=40 at %, I=17 at %)

The optical properties, which were measured in this case in the range of visible light, such as absorption, transmission, reflection, and also the color values upon reflection and transmission, are found in Table 3, and the results of the analysis of the antimicrobial properties of the coating are found in Tables 5 and 6.

Because of the large number of experiments carried out, hereafter only the ranges are set forth in the boundaries of which the invention may be executed on the basis of Tables 1 to 6, in addition to the above-described exemplary embodiment having the composition $Cu_{0.07}Si_{0.35}N_{0.23}O_{0.35}$.

In Table 1, the absolute values of the quantity components of the elements contained in the layer for the ranges 1 and 2, which are advantageous according to the invention, and also the values of the above-listed examples are specified.

TABLE 1

| Element | Example | Range 1 | Range 2 |
|---------|---------|---------|---------|
| Cu | 7 at % | 6-8 at % | 2-15 at % |
| Si | 35 at % | 33-37 at % | 25-45 at % |
| N | 23 at % | 21-25 at % | 15-31 at % |
| O | 35 at % | 32-38 at % | 25-45 at % |

In contrast, in Table 2, the ranges of the ratio numbers G, H, I which are to be selected according to the invention for setting good antimicrobial or favorable optical properties, respectively, are shown. Although the ranges 1' and 2' lie within the ranges 1 and 2, respectively, the former, as explained in greater detail hereafter, are surprisingly better suitable for the targeted setting of the desired layer properties than if the setting is performed solely according to the quantity components.

TABLE 2

| Ratio | Example | Range 1' | Range 2' |
|-------|---------|----------|----------|
| I = Cu/(Cu + Si) | 17 at % | 15-20 at % | 5-30 at % |
| H = N/(N + O) | 40 at % | 35-45 at % | 30-50 at % |
| G = (Cu + Si)/(total) | 42 at % | 37-47 at % | 32-52 at % |

It is to be noted in this regard that the formation of $SiO_2$ and $Cu_2O$ phases, in which Cu(I) is present, was detected with respect to the phase formation actually occurring in the layer according to the invention. In contrast thereto, in the event of an excessively high oxygen component below the N/(N+O) limits indicated in Table 2, under range 2', for example, at H≤25 at %, an increasing component of CuO phases occurs. In this case, such compounds which contain copper (II) have proven to be less antimicrobial in the experiments. In the event of an excessively high N/(N+O) ratio, the formation of nitridic copper compounds and/or elementary copper during the coating process to an increased extent is in turn suspected. Surprisingly, it has been shown here that in particular copper (I) compounds display very good antimicrobial effect, also on dry surfaces.

It has also surprisingly been shown in this case that if a specific N/(N+O) ratio is set in the layer, a majority of the copper, or even all of the copper, was present in the layer in monovalent form, in particular as $Cu_2O$ and/or $Cu_3N$. This was additionally promoted by the setting of a specific Si/(Cu+Si) ratio in the layer (see Table 6). Thus, with high I values, for example, in the range from 20 to 30 at %, very thin antimicrobially active layers can be deposited, but such layers display a significantly higher shift of the absorption and/or color values in relation to uncoated glass substrates. In contrast, upon selection of a low I value, for example, in the range from 5 to 15 at %, comparatively thick layers can also be deposited without negatively influencing the optical properties.

Similar experiments using a (metallic, oxidic, nitridic, or oxynitridic) mixed target, as mentioned above, having a target composition, $I_T$=Cu/(Cu+Si)=15 to 30 at %, in place of the silicon target and the copper target have led to a similar result.

The optical properties in the visible wavelength range, which were measured at a layer thickness of approximately 40 nm on 4-mm-thick soda-lime glass according to CIE Lab System, using light type C, at an observation angle of 2°, are listed accordingly in Table 3.

TABLE 3

|  | Example | Range 1' | Range 2' |
| --- | --- | --- | --- |
| Absorption | 2.8 at % | 1-4 at % | 0-6 at % |
| Transmission | 82.8 at % | 79-90 at % | 70-95 at % |
| Reflection | 14.4 at % | 9-16 at % | 4-20 at % |
| Color values Refl. a*/b* | −0.3/−6.0 | −1.5-0/−7.2--4.5 | −4-2/−8.5--2 |
| Color values Transm. a*/b* | −0.9/3.2 | −1.3--0.5/1.5-5.5 | −3-2/−1-8 |

Antimicrobially active layers according to the invention were able to be deposited within the layer thickness ranges listed in Table 4. It was determined in this case that with extremely thin layers, for example, between 1 to 5 nm, the antimicrobial effect can become less with time, for example, due to washing off. This effect can be counteracted, however, for example, by simultaneously increasing the ratio I to values between 20 and 30 at % and/or setting the value G to values between 47 and 52 at %. Therefore, such layers still have a sufficient bactericidal effect of >75% and only a slight optical deviation in relation to uncoated normal glass (comparison glass).

Vice versa, with large layer thicknesses, for example, from 80 to 130 nm, the deviation of the optical properties from the comparison glass (absorption, color values) grows, because of which such coatings are more suitable for objects which are opaque or insensitive with respect to the change of the optical properties thereof. In the boundary regions of the range B, i.e., 5 to 10 nm, or 80 to 130 nm, layers can be set to very good optical properties, or layers can be set to very good antimicrobial properties, respectively, which are simultaneously adapted in color, for example, by setting the copper content up to 15 at % and/or by adding a doping element. In contrast, in the entire layer thickness range A upon selection of the layer composition according to ranges 1 and 1', layers were able to be deposited, which have both very good optical properties and also very good antimicrobial properties (see Table 6).

TABLE 4

|  | Range A | Range B | Range C |
| --- | --- | --- | --- |
| Layer thickness | 10-50 nm | 5-80 nm | 1-130 nm |

Table 5 provides a compilation of the antimicrobial, in particular bactericidal and/or fungicidal properties with respect to the species listed in the column "germ". The present specifications relate in this case to the lowest measured bacterial elimination in the range A, B, C, and/or to the bacterial elimination in the case of a layer composition according to the example.

For this purpose, various layers having a layer composition according to range 1 were tested for all elements according to the above-described test method.

TABLE 5

| Germ | Example [%] | Range A [%] | Range B [%] | Range C [%] |
| --- | --- | --- | --- | --- |
| S. aureus (gram+) | 87 | >80 | >75 | >45 |
| E. faecalis (gram+) | 82 | >80 | >75 | >45 |
| E. coli (gram−) | 90 | >85 | >80 | >50 |
| A. Baumannii (gram−) | 100 | >85 | >80 | >50 |
| C. albicans (fungus) | 71 | >65 | >60 | >40 |

The selected germs for the antibacterial or the antifungicidal test, respectively, which was also performed, are representative in this case. Of course, the antimicrobial effect is not only restricted to these listed germs. Table 6 shows a comparison of the antimicrobial efficacies and of optical test results for layer compositions in the range 1' (or 1) of Table 2 with respect to the ratio numbers I=Cu/(Cu+Si) and H=N/(N+O), with a layer thickness in the range B of Table 5.

It was shown in this case that layers having I<15 at % and/or H<35 at % do still have good optical properties, but are comparatively weakly antimicrobial. Vice versa, layers having I>20 at % and/or H>45 at % display good antimicrobial properties, but only have limited use for optical purposes as a result of the greater deviations, in particular the absorption of visible light and the color values. A result which is very good both with respect to the optical properties and also with respect to the antimicrobial properties may be achieved within the boundaries I=15-20 at %, in particular if simultaneously H=35-45 at %.

TABLE 6

| Quantity ratio | Bacterial elimination [%] | Transm. [%] | Refl. [%] | Color values Reflection a*/b* | Color values Transmission a*/b* |
| --- | --- | --- | --- | --- | --- |
| I = 15-20 at % | >75 | 79-90 | 9-16 | −1.5-0/−7.2--4.5 | −1.3--0.5/1.5-5.5 |
| I < 15 at % | <45 | 79-90 | 9-16 | −1.5-0/−7.2--4.5 | −1.3--0.5/1.5-5.5 |
| I > 20 at % | >75 | <79 | >16 | <−1.5/<−7.2 | <−1.3/>5.5 |
| H = 35-45 at % | >75 | 79-90 | 9-16 | −1.5-0/−7.2--4.5 | −1.3--0.5/1.5-5.5 |
| H < 35 at % | <45 | 79-90 | 9-16 | −1.5-0/−7.2--4.5 | −1.3--0.5/1.5-5.5 |

The examples and combinations of various embodiments set forth in the present description are only used to illustrate individual aspects, but do not restrict the scope of protection of the invention, because other combinations are also possible, and all mentioned examples and embodiments are fundamentally combinable with one another and fall under the scope of protection of the invention, as long as this is not contradictory, which is readily apparent to a person skilled in the art.

The invention claimed is:

1. An object having a coating arranged on at least one surface of the object, which comprises at least one antimicrobially active layer having an antimicrobial agent, wherein the antimicrobial agent comprises:
   at least one of a copper (Cu) (I) compound and a copper (Cu) (II) compound,
   wherein the at least one antimicrobially active layer further contains at least 25 at % silicon (Si), and nitrogen (N) and oxygen (O), and a doping element D, and
   a doping element D, characterized in that in the at least one antimicrobially active layer is at least 40 at % non-metal and has, a ratio of concentrations (in at %) of $G = (Cu+Si)/(Cu+Si+N+O+D)$ wherein $32 \leq G \leq 52\%$ is present and the doping element is in a range from $0 \leq D \leq 15$ at %.

2. The object according to claim 1, characterized in that the antimicrobial agent is an oxide, an oxynitride, or a nitride.

3. The object according to claim 1, characterized in that the antimicrobial agent is $Cu_2O$ and/or $Cu_3N$.

4. The object according to claim 1, characterized in that the at least one antimicrobially active layer comprises at least 2 at % copper.

5. The object according to claim 1, characterized in that at least one intermediate layer is arranged between the at least one antimicrobially active layer and the at least one surface of the object.

6. The object according to claim 5, characterized in that the at least one intermediate layer comprises an antireflective layer consisting of at least one high-refractive-index and one low-refractive-index layer film.

7. The object according to claim 1, characterized in that a hydrophobic and/or oleophobic layer is arranged on a layer surface facing away from the object.

8. The object according to claim 1, characterized in that the object is a glass.

9. The object according to claim 1, characterized in that the doping element D comprises at least one of the following metals: Ag, Al, Cd, Sn, As, Fe, Mn, Ni, Zn, Cr.

10. A method for coating an object with an antimicrobial layer comprising the following steps:
    providing a sputtering facility having at least one copper-containing target;
    introducing the object into the sputtering facility;
    creating a vacuum in the sputtering facility;
    introducing an inert sputtering gas and a reactive gas containing oxygen and/or nitrogen;
    igniting and maintaining a sputtering discharge at the copper-containing target;
    setting the reactive gas flow so that a layer containing a copper (I) compound and/or a copper (II) compound is deposited on the object, characterized in that the target is a target containing copper and silicon wherein a ratio of amounts (in at %)

$I_T = Cu/(Cu+Si)$ is provided in the target in a range from $5 \leq I_T \leq 40\%$.

11. The method according to claim 10, characterized in that the target is a CuSi target, a copper silicon oxide target, a copper silicon nitride target, or a copper silicon oxynitride target.

12. A method for coating an object with an antimicrobial layer comprising the following steps:
    providing a sputtering facility having at least one copper-containing target;
    introducing the object into the sputtering facility;
    creating a vacuum in the sputtering facility;
    introducing an inert sputtering gas and a reactive gas containing oxygen and/or nitrogen;
    igniting and maintaining a sputtering discharge at the copper-containing target;
    setting the reactive gas flow so that a layer containing a copper (I) compound and/or a copper (II) compound is deposited on the object,
    characterized in that the target is a copper target, a copper nitride target, a copper oxide target, and/or a copper oxynitride target, and the sputtering facility furthermore comprises at least one silicon target, a silicon oxide target, a silicon nitride target, and/or a silicon oxynitride target, wherein the method comprises the following further steps:
    igniting and maintaining a sputtering discharge at the copper containing target
    igniting and maintaining a sputtering discharge at the silicon-containing target
    setting the sputtering rates at the copper target and at the silicon-containing target to set a ratio of amounts (in at %)

$I = Cu/(Cu+Si)$ wherein $5 \leq I \leq 30\%$ in the target.

13. The method according claim 10, characterized in that the compound which is deposited is $Cu_2O$ and/or $Cu_3N$.

14. The method according to any one of claims 10, 11, 12, and 13, characterized
- by a reactive gas containing a mixture of oxygen and nitrogen, and
- by setting the partial pressure of the oxygen gas and the partial pressure of the nitrogen gas in the mixture of oxygen and nitrogen to set a ratio of amounts (in at %)

$H=N/(N+O)$ wherein $30 \leq H \leq 50\%$ in the antimicrobial layer.

* * * * *